(12) United States Patent
Haaland

(10) Patent No.: US 9,403,757 B2
(45) Date of Patent: Aug. 2, 2016

(54) PREPARATION OF INTERMEDIATES OF X-RAY CONTRAST AGENTS

(71) Applicant: GE Healthcare AS, Oslo (NO)

(72) Inventor: Torfinn Haaland, Lindesnes Fabrikker (NO)

(73) Assignee: GE Healthcare AS, Nycoveien (NO)

( * ) Notice: Subject to any disclaimer, the term of this patent is extended or adjusted under 35 U.S.C. 154(b) by 0 days.

(21) Appl. No.: 14/437,430

(22) PCT Filed: Oct. 24, 2013

(86) PCT No.: PCT/US2013/066487
§ 371 (c)(1),
(2) Date: Apr. 21, 2015

(87) PCT Pub. No.: WO2014/074315
PCT Pub. Date: May 15, 2014

(65) Prior Publication Data
US 2015/0274645 A1    Oct. 1, 2015

(30) Foreign Application Priority Data

Nov. 12, 2012 (EP) .................................. 12192193

(51) Int. Cl.
| | |
|---|---|
| *C07C 237/46* | (2006.01) |
| *A61K 49/04* | (2006.01) |
| *C07C 231/12* | (2006.01) |
| *C07C 231/14* | (2006.01) |

(52) U.S. Cl.
CPC ........... *C07C 237/46* (2013.01); *A61K 49/0438* (2013.01); *C07C 231/12* (2013.01); *C07C 231/14* (2013.01)

(58) Field of Classification Search
CPC .. C07C 237/46; C07C 231/14; C07C 231/12; A61K 49/0438
See application file for complete search history.

(56) References Cited

U.S. PATENT DOCUMENTS

| | | | |
|---|---|---|---|
| 7,244,864 B2 * | 7/2007 | Anelli .................. | C07C 227/04 560/20 |
| 8,920,780 B2 * | 12/2014 | Thaning ............ | A61K 49/0433 424/9.1 |
| 2011/0021822 A1 | 1/2011 | Askildsen et al. | |
| 2011/0021828 A1 * | 1/2011 | Homestad ............ | B01D 61/027 564/153 |

OTHER PUBLICATIONS

International Search Report and Written Opinion regarding International Appliation No. PCT/US2013/066487, mail date Feb. 21, 2014, 8 pages.

\* cited by examiner

*Primary Examiner* — Shailendra Kumar

(57) ABSTRACT

The present invention relates to a process for the preparation of iodinated X-ray contrast agents and in particular to key intermediates thereof. It particularly relates to an improved process for preparation of 5-acetamido-N,N'-bis(2,3-dihydroxypropyl)-2,4,6-triiodoisophthalamide (Compound A) or N,N'-bis(2,3-dihydroxypropyl)-5-formamido-2,4,6-triiodo-isophthalamide (Compound C), which are intermediates in the industrial preparation of non-ionic X-ray contrast agents. More particularly the invention provides a process for deacylation of the acylated hydroxyl groups of an intermediate compound of Compound A and Compound C.

11 Claims, No Drawings

PREPARATION OF INTERMEDIATES OF X-RAY CONTRAST AGENTS

This application is a filing under 35 U.S.C. 371 of international application number PCT/US2013/066487, filed Oct. 24, 2013, which claims priority to European application number 12192193.6, filed Nov. 12, 2012, the entire disclosures of each of which are hereby incorporated by reference.

The present invention relates to a process for the preparation of iodinated X-ray contrast agents and in particular to key intermediates thereof. It further relates to an improved process for preparation of 5-acetamido-N,N'-bis(2,3-dihydroxypropyl)-2,4,6-triiodoisophthalamide (Compound A) or N,N'-bis(2,3-dihydroxypropyl)-5-formamido-2,4,6-triiodo-isophthalamide (Compound C), intermediates in the industrial preparation of non-ionic X-ray contrast agents. In particular, it relates to a process for deacylation of the acylated hydroxyl groups of an intermediate of these compounds. Further, the invention relates to a process for preparing contrast agents such as Iodixanol, Iohexol and Ioforminol, useful in X-ray imaging.

For the last 50 years the field of X-ray contrast agents has been dominated by soluble iodine containing compounds. Commercial available contrast media containing iodinated contrast agents are usually classified as ionic monomers such as diatrizoate (Gastrografen™), ionic dimers such as ioxaglate (Hexabrix™), nonionic monomers such as iohexol (Omnipaque™), iopamidol (Isovue™), iomeprol (Lomeron™) and the non-ionic dimer iodixanol (Visipaque™). The most widely used commercial non-ionic X-ray contrast agents such as those mentioned above are considered safe. Contrast media containing iodinated contrast agents are used in more than 20 million of X-ray examinations annually in the USA and the number of adverse reactions is considered acceptable. Non-ionic X-ray contrast agents constitute a very important class of pharmaceutical compounds produced in large quantities. 5-[N-(2,3-dihydroxypropyl)-acetamido]-N,N'-bis(2,3-dihydroxypropyl)-2,4,6-triiodo-isophthalamide (Iohexol) and 1,3-bis(acetamido)-N,N'-bis[3,5-bis(2,3-dihydroxypropyl-aminocarbonyl)-2,4,6-triiodophenyl]-2-hydroxypropane (Iodixanol) are important examples of such compounds. For example, Iodixanol, marketed under the trade name Visipaque®, is one of the most used agents in diagnostic X-ray procedures. It is produced in large quantities by GE Healthcare, Norway.

The manufacture of non-ionic X-ray contrast media involves the production of the chemical drug, the active pharmaceutical ingredient (API), i.e. the contrast agent, followed by the formulation into the drug product, herein denoted the X-ray composition.

The industrial production of Iodixanol and Iohexol involve multistep chemical syntheses, wherein the last steps are shown in Scheme 1 below, starting from 5-amino-N,N'-bis(2,3-dihydroxypropyl)-2,4,6-triiodoisophthalamide, named Compound B. Preparation of Compound B is well described in the state of the art. See also U.S. Pat. No. 6,974,882.

Scheme 1

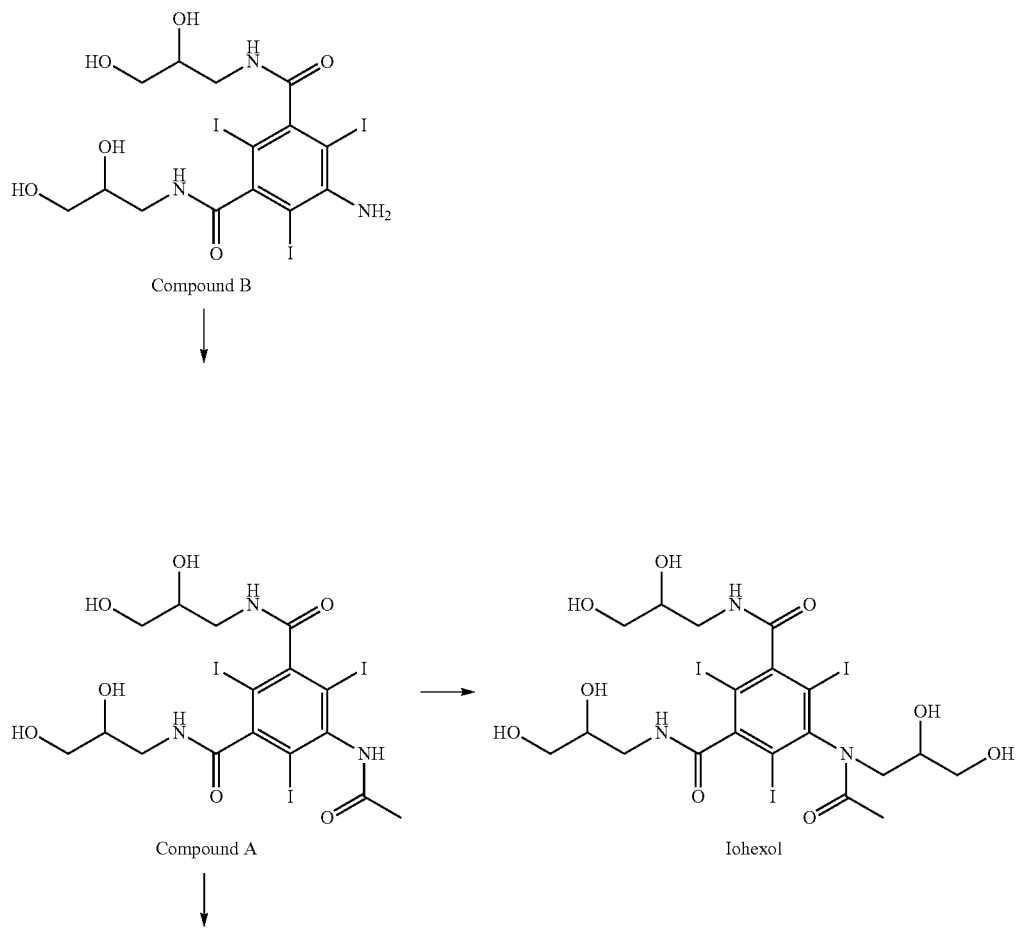

-continued
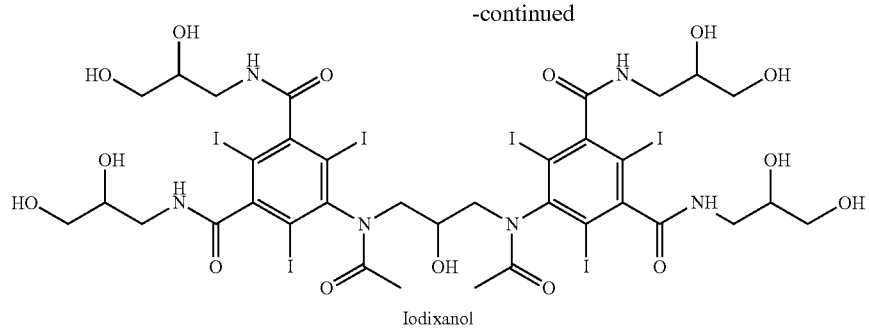
Iodixanol
Also the compound named Ioforminol, 5,5'-(2-Hydroxypropane-1,3-diyl)bis(formylazanediyl)bis($N^1$,$N^3$-bis(2,3-dihydroxypropyl)-2,4,6-triiodoisophthalamide), can be prepared from Compound B as shown in scheme 2 below.
Scheme 2:
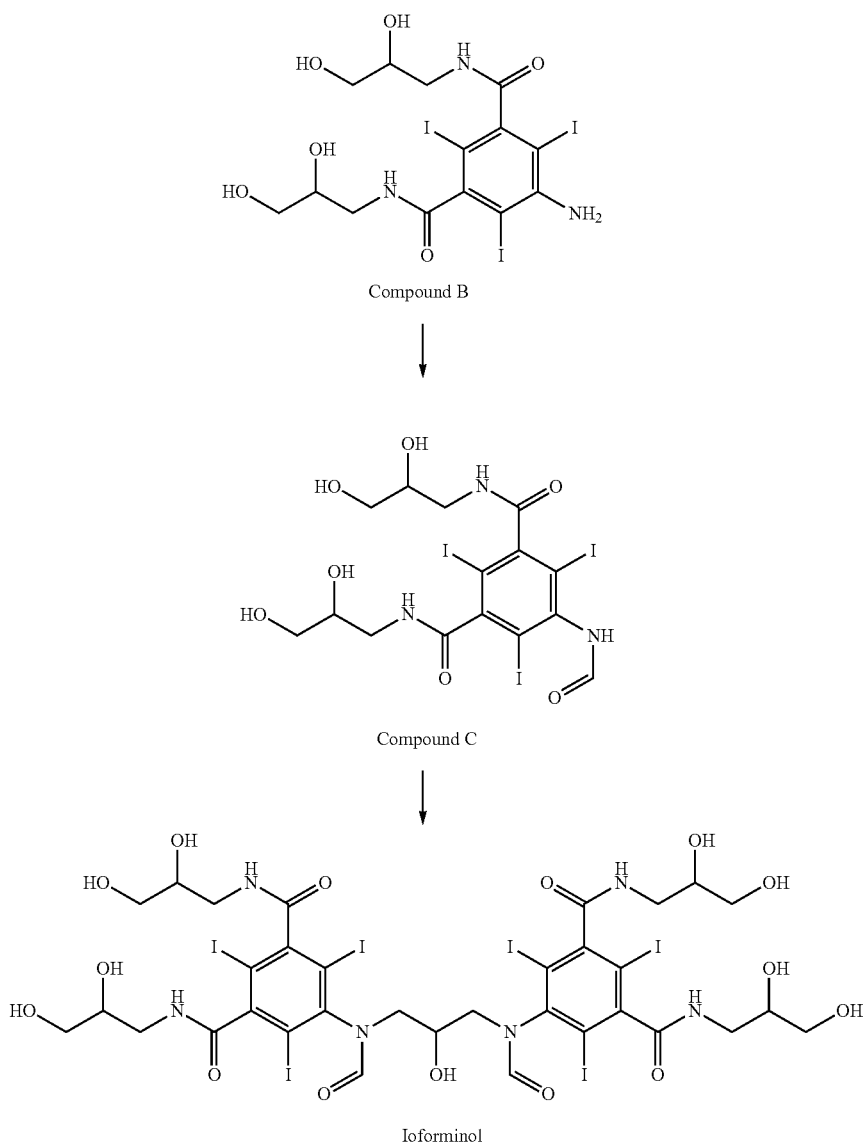

To reduce the cost of the contrast agent and the final product, it is critical to optimize each synthetic step to obtain an optimal yield and to minimize the production of impurities. Even a small improvement in reaction design can lead to significant savings in a large scale production.

An improved process has been sought for preparation of N-acylated monomeric compounds from compound B, such as the N-acetylated compound 5-acetamido-N,N'-bis(2,3-dihydroxypropyl)-2,4,6-triiodoisophthalamide, named Compound A herein, and the N-formylated compound N,N'-bis(2,3-dihydroxypropyl)-5-formamido-2,4,6-triiodoisophthalamide, named compound C herein.

In the acetylation step of the industrial scale synthesis of Iohexol and Iodixanol, 5-amino-N,N'-bis(2,3-dihydroxypropyl)-2,4,6-triiodoisophthalamide (Compound B) is acetylated to produce 5-acetylamino-N,N'-bis(2,3-dihydroxypropyl)-2,4,6-triiodoisophthalamide (Compound A) using acetic anhydride as the acetylating reagent. We have now found that Compound A can be prepared from Compound B in an optimized process wherein the generation of certain impurities is significantly reduced.

The problem to be solved by the present invention may be regarded as the provision of optimizing the process for preparation of N-acylated monomeric compounds which are intermediates for X-ray imaging contrast agents, particularly preparation of Compound A and Compound C.

In the acylation reaction of Compound B, the amino function is acylated, either acetylated or formylated, depending on which end product to prepare. But in addition, also the four hydroxyl groups of Compound B are acylated. See Scheme 3. The acylated hydroxyl groups of the intermediate named Compound B2 are undesirable and need to be deacylated following the acylation reaction. The instant invention is directed to a process for deacylation of the undesired acylated groups of compound B2 generated during the acylation step.

Scheme 3:

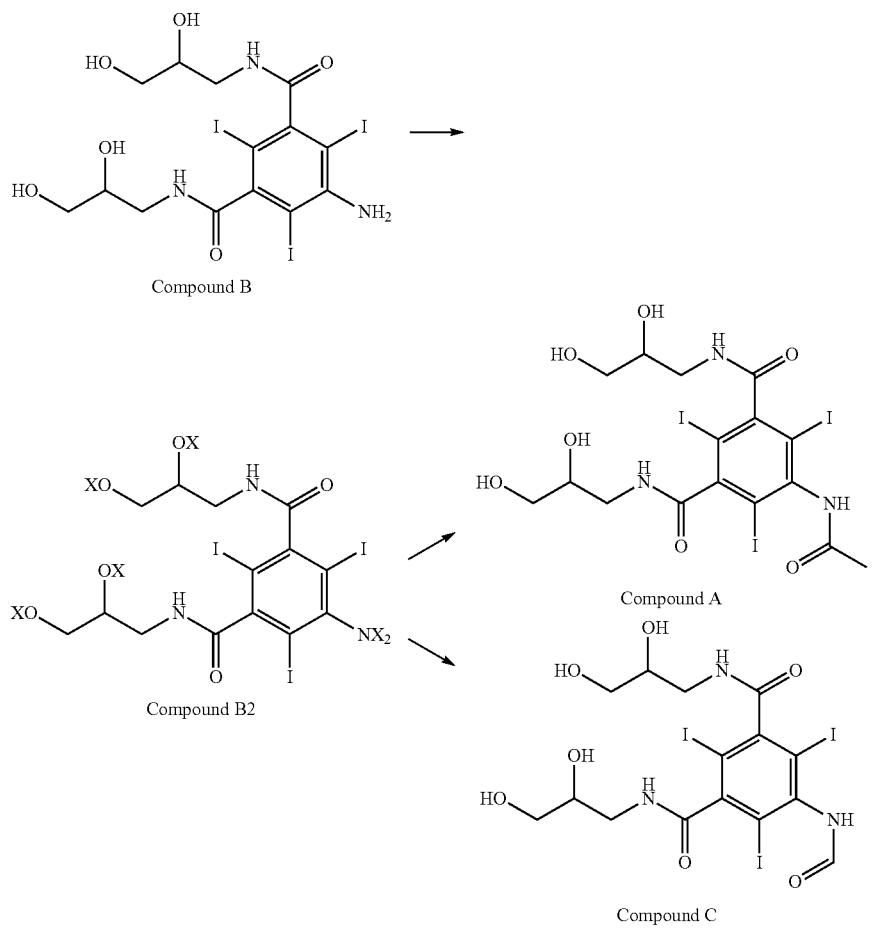

In Compound B2 X denotes hydrogen or an acyl group.

A process for preparing Compound A from Compound B, including a deacetylation of the O-acetylated groups of Compound B2 is known from e.g. EP2281811A1 of GE Healthcare AS, directed to a continuous process comprising deacetylating the acetylated hydroxyl groups in a first reactor at a pH between 11 and 12 by addition of a suitable base such as aqueous sodium hydroxide.

In the preparation of Compound A from Compound B, the first step is acetylation. The next step is deacetylation to remove O-acetyl groups that are formed during the acetylation reaction. Using the process of the prior art, one of the main impurities in the crude Compound A prepared has now been found to be the Compound 1 shown below:

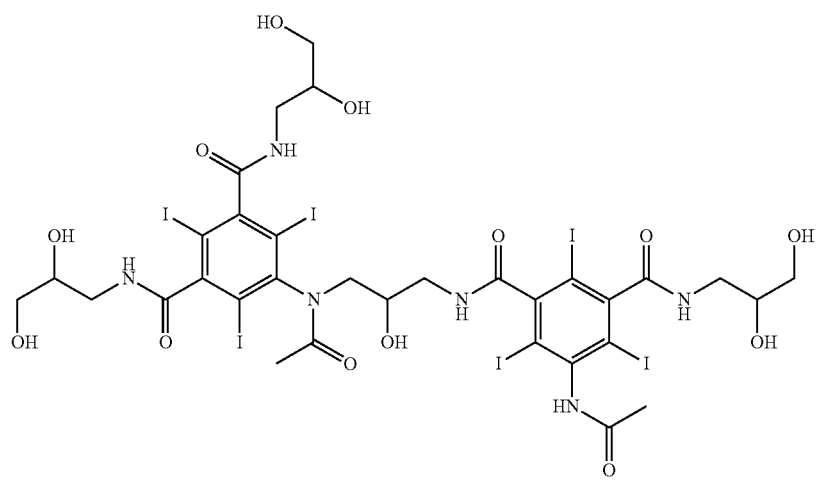

Compound 1

Compound 1: 5-acetamido-N1-(3-(N-(3,5-bis((2,3-dihydroxypropyl)carbamoyl)-2,4,6-triiodophenyl)acetamido)-2-hydroxypropyl)-N3-(2,3-dihydroxypropyl)-2,4,6-triiodoisophthalamide Detailed mechanistic studies have shown that Compound 1 is formed via several steps during the prior art process. Normally, in the deacylation step, sodium hydroxide (50%, aq) is added to the solution containing over-acylated Compound B, i.e. to the compound named Compound B2 in Scheme 2. It has now surprisingly been found that the deacylation can be done in an alternative way wherein the generation of the impurity called Compound 1 is significantly reduced. The alternative identified is to add the solution of Compound B2 to a deacylating agent, such as a base.

Accordingly, in a first aspect the invention provides a process for preparation of an N-acylated monomeric compound selected from Compound A and Compound C comprising a step wherein Compound B2,

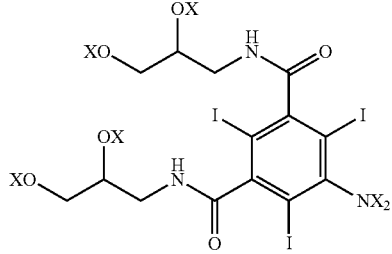

Compound B2 wherein each X individually denotes a hydrogen or an acyl group;
is subjected to deacylation of the acylated hydroxyl groups by adding the Compound B2 to an aqueous solution of a deacylating agent.

In one embodiment, the Compound B2 is added to the deacylating agent in the form of a solution. In another embodiment, the Compound B2 is in solid form when added to the deacylating agent. Preferably a solution of Compound B2 is used.

The X-group is either hydrogen or acyl, provided that at least one of the X-groups attached to the nitrogen is an acyl group. The acyl group is selected from formyl and acetyl and is preferably acetyl. The main component of Compound B2 is preferably Compound B3

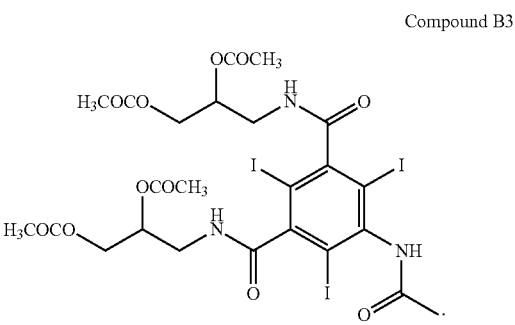

Compound B3

In one embodiment, Compound B2 is compound B3.

Compared to the state of art process, rather than adding the deacylating agent, normally a base, to the Compound B2, the Compound B2 is added to a deacylating agent. The main advantage of the alternative deacylation process of the invention is reduction of generation of certain impurities. Particularly, for the preparation of compound A according to the invention a reduction of the generation of the impurity Compound 1 and less generation of heat during the deacylation process is achieved. Compound 1 is an impurity which is difficult to remove from the crude product of Compound A. For instance, this will not be removed by crystallisation. The process of the invention, providing a significant reduction in the amount of generated Compound 1 accordingly has an effect particularly on the yield, when using the generated Compound A in further synthesis, e.g. in the preparation of a contrast agent, such as Iohexol or Iodixanol.

It has been found that the formation of impurity Compound 1, in the state of art process, goes via several steps. The latest two steps take place during the deacylation step. First an epoxide, Compound 2, is formed.

Compound 2

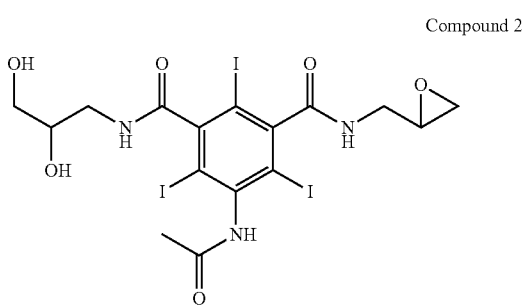 [SMILES: CC(=O)Nc1c(I)c(C(=O)NCC(O)CO)c(I)c(C(=O)NCC2CO2)c1I]

This epoxide is reactive and secondly this reacts with the prepared anionic Compound A molecule under basic conditions, as shown below, generating the impurity Compound 1.

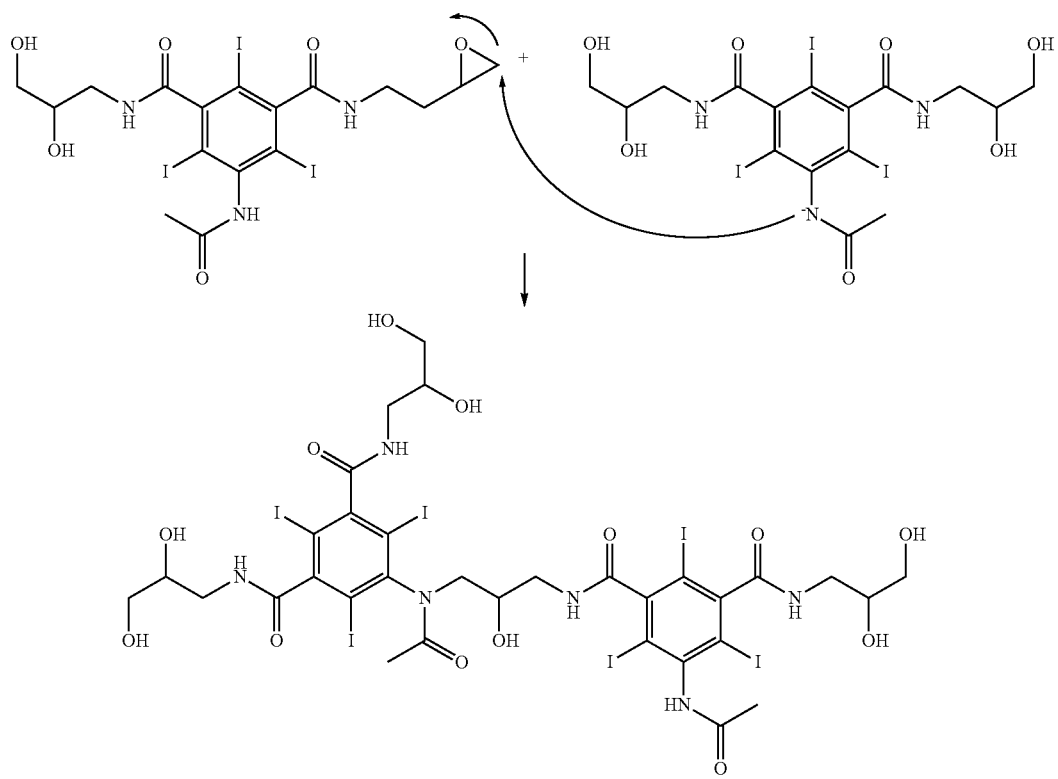

This step for the formation of Compound 1 is a dimerisation reaction and since this is a reaction between two molecules this step is consequently found to be concentration dependent. Accordingly, it has been assumed that if the deacylation step takes place under more diluted conditions, the formation of compound 1 will be suppressed. In the state of art process, sodium hydroxide (50%, aq) is added to the acidic solution containing over-acylated Compound A (i.e. compound B2).

The intuitive solution to the problem, when having identified the Compound 1 impurity and how it is generated and assuming that more dilute conditions are needed, is that the acidic solution of Compound B2, could have been diluted with much more solvent, such as methanol and water, prior to the deacylation step to suppress formation of Compound 1. However, it has been found that such solution to the problem has the drawback of reducing production capacity.

A feasible and cost-efficient alternative, as stated in the first aspect of the invention, has surprisingly been found to be addition of Compound B2, such as the acidic solution of Compound B2, to an aqueous solution of a deacylating agent. This alternative will generate less heat during the deacylation step, compared to when the deacylating agent is added to a solution of Compound B2, because much of the dilution heat is removed before the deacylation starts. Therefore, the deacylation can be done under milder temperature conditions. The most important difference from the state of art deacylation process is the concentration profile of the substrate compound B2 during the deacylation. The concentration will be much lower in the claimed deacylation process compared with the state of the art process, and as a consequence, the level of generated Compound 1 is much lower.

Prior to the deacylation of the acylated hydroxyl groups of Compound B2 an acylation of Compound B takes place.

Hence, in this embodiment, the process includes such step and the invention provides a process for preparation of an N-acylated monomeric compound selected from Compound A and Compound C comprising a first step of acylating Compound B to prepare compound B2;

followed by a step wherein Compound B2 is subjected to deacylation of the acylated hydroxyl groups by adding the Compound B2 to an aqueous solution of a deacylating agent.

The acylation of Compound B may be effected by any convenient method, e.g. by use of anhydrides and acids. When the acylation step is a formylation to provide Compound C any convenient method may be used, e.g. by use of activated formic acid such as mixed anhydrides as the formylating agent. Mixed anhydrides can be prepared by a variety of methods described in the literature. A convenient method of preparing mixed anhydrides is to add a carboxylic acid anhydride to an excess of acetic acid under controlled temperature. Preferably, a mixture of formic acid and acetic anhydride is used in the formylation step. As a result of the formylation step using mixed anhydrides, Compound B2 will be a mixture of different compounds with both formyl and acetyl protecting groups. Varies degree of O-formylation is seen, but a high degree of N-formylation takes place, ensuring a high yield of the N-formylated Compound C after deacylation. When the acylation step is an acetylation to provide Compound A, acetic acid and acetic acid anhydride is preferably used. In this embodiment the main component of Compound B2 is Compound B3, wherein all the acylated OH groups are acetylated.

There is no particular restriction upon the nature of the deacylating agent used, and any deacylating agent commonly used in conventional reactions may equally be used here. Examples of suitable deacylating agents include aqueous inorganic bases including alkali metal carbonates, such as sodium carbonate, potassium carbonate or lithium carbonate; and alkali metal hydroxides, such as sodium hydroxide, potassium hydroxide or lithium hydroxide. Of these, the alkali metal hydroxides, particularly sodium hydroxide or potassium hydroxide, and most preferably sodium hydroxide are preferred.

The deacylating agent is in one embodiment diluted with water prior to adding this to the solution of Compound B2. In a preferred embodiment, the deacylating agent is sodium hydroxide, and if using this a 50% aqueous sodium hydroxide solution is e.g. added to water in a 1:1 to 1:5 ratio, such as in a 1:1 to 1:2 ratio. Preferably, the concentration of base, such as NaOH used, is about 10-50 w/w %, more preferably 20-25%. When starting the addition of the compound B2 solution to the deacetylating agent the pH of the mixed solution will be about 14, and this is reduced to about 11-13 as the addition of the solution of Compound B2 is added and ended. The addition is done over a period of e.g. 0.5-2 hours. The addition to the deacylating agent is done either in several small portions over this period, or more preferably continuously, adding the solution of Compound B2 slowly and gently under stirring. Under these conditions, only the desired NH-acyl group survives the hydrolysis and remains acylated. In addition, the generation of impurity Compound 1 is minimal.

The process will generate little heat during the deacylation step, because much of the dilution heat is removed before the deacylation starts. Hence, in total there is a smaller temperature increase compared to the process of the prior art. Therefore, the deacylation can be done under milder temperature conditions. During the addition of the Compound B2 solution to the solution of the deacylating agent, the temperature increases e.g. from a start temperature of 20-35° C. to an end temperature 50-60° C. depending e.g. on what kind of equipment is used. After the addition is finalized the solution may be further diluted, preferably with water, to obtain the desired concentration before crystallisation.

The deacylation reaction is preferably effected in the presence of a solvent, and Compound B2 is solved in such before addition of a solution of compound B2 to the deacylating agent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol or ethanol; and water. Of these, alcohols, particularly methanol, or a mixture of water and one or more alcohols are preferred. In one embodiment, particularly for the preparation of Compound C, Compound B2 is not solved in any solvent prior to addition to the deacylating agent and hence this is added as a solid compound.

After the deacylating step has been performed, i.e. when all the Compound B2 has been added to the deacylating agent, an acid is added to reduce pH to lower the solubility of the prepared Compound A or Compound C, to provide a thicker suspension and hence start the precipitation of Compound A or Compound C. The acid added is a water soluble strong inorganic acid and is preferably selected from the group of sulphuric acid, nitric acid and hydrochloric acid and is most preferably hydrochloric acid. The pH is reduced to 2.0-8.0 such as 5.0-8.0 and preferably to about 7, under stirring for a period to allow the precipitation to completion, such as for at least half an hour. In one embodiment, the reaction solution is seeded with Compound A or Compound C, depending on which compound to prepare, before, during or after the pH adjustment. This suspension is preferably left under stirring at reduced temperature, such as 10-25° C., preferably about 20° C. for 5-20 hours, such as for about 10 hours. The Compound A product is then collected and optionally purified. In one embodiment the process comprises such further step of collecting the product preferably by filtration, e.g. by using a nutch filter, such as a vacuum nutch filter or pressure nutch, or a combination thereof, also optionally combined with heating. The product is preferably subsequently washed, preferably with the same solvent as used in the deacylating step, such as methanol, in one or more portions, such as in 1 to 5 portions and preferably with 3 portions, and then optionally being dried in suitable drying equipment. Accordingly, in a further embodiment of the invention, after deacylation the prepared Compound A or Compound C product is collected and this is optionally purified, such as by crystallisation.

The instant process provides the Compound A and Compound C with consistent quality and yield. The procedure has been repeated multiple times and provides purity above 99.5%, both small scale and large scale, such as in 100 kg scale. Particularly, the amount of the impurity Compound 1 generated when using the process of the invention preparing Compound A, is minimal and the dried product of Compound A comprises 0.08% or less, or preferably less than 0.05% and more preferably less than 0.025% of Compound 1. In a further aspect, the invention provides a dried product of Compound A comprising 0.08% or preferably less than 0.05 weight % and more preferably less than 0.025 weight % of the impurity Compound 1. Such product is obtainable when using the process of the invention. The fact that considerably less Compound 1 is generated when using the process of the invention than when using the state of the art process, is particularly important when using the prepared Compound A in the further synthesis of contrast agents. For instance, a reduction from 0.09 weight % to 0.02 weight % of generated Compound 1 in the purified Compound A will increase the overall conversion of prepared Iodixanol with 1-5%, having a significant economic benefit.

Processes which take the Compound A or Compound C as prepared by the claimed process and react this further, e.g. to produce a contrast agent such as Iodixanol, Iohexol or Ioforminol, are hence deemed to fall within the scope of the invention. Hence, in a further aspect the invention provides a process for preparing a contrast agent, wherein this comprises the process for preparation of Compound A or Compound C as described in the first aspect. Such process could comprise the additional steps of alkylation or bis-alkylation (dimerization) to provide Iohexol or Iodixanol respectively, or to provide Ioforminol if doing a bisalkylation of Compound C. E.g. in a final step for preparation of Iodixanol a bis-alkylation via a 2-hydroxypropane bridge takes place. This step may be carried out as described in European patent 108638 and WO 98/23296, for example using epichlorohydrin, 1,3-dichloro-2-hydroxypropane or 1,3-dibromo-2-hydroxypropane as the dimerization agent. This dimerization is preferably effected in the presence of an acid binding agent, for example an organic or inorganic base; an alkali metal alkoxide such as sodium methoxide or an alkali metal hydroxide such as sodium and potassium hydroxide may be used as base.

The compounds as prepared by the claimed process, hence the compounds A and C and the final contrast agents, comprise optical active isomers and will exist in several isomeric forms due to chiral carbon atoms. In addition, the compounds exhibit exo/endo isomerism due to the restricted rotation of the N—CO bond in the acyl function caused by the proximity of the bulk iodine atom. Both preparation of enantiomerically pure products as well as mixtures of optical isomers are encompassed by the process of the invention.

The compounds prepared according to the invention may be used as contrast agents and may be formulated with conventional carriers and excipients to produce diagnostic contrast media. Thus viewed from a further aspect the invention provides a diagnostic composition comprising a contrast agent prepared according to the process of the invention, together with at least one physiologically tolerable carrier or excipient, e.g. in aqueous solution for injection optionally together with added plasma ions or dissolved oxygen. The contrast agent composition of the invention may be in a ready to use concentration or may be a concentrate form for dilution prior to administration. Hence, the invention further embraces use of a contrast agent prepared according to the process of preparation, and a diagnostic composition containing such, in X-ray contrast examinations.

The invention is illustrated with reference to the following non-limiting examples.

EXAMPLES

Example 1

Acetylation of Compound B Followed by Deacetylation by State of Art Process and Process of the Invention to Prepare Compound A Compound B was acetylated in a mixture of acetic anhydride and acetic acid. Paratoluene sulfonic acid (PTSA) was used as a catalyst. After acetylation, the solution was concentrated under reduced pressure, and then methanol and water was added prior to the deacetylation step. This solution (Compound B2 solution) was divided into two equal parts. One part was deacetylated according to current practice and the other part was deacetylated according to the process of the invention.

Comparative Process of the State of the Art:
Sodium hydroxide (50%, 150 mL) was added to the solution containing Compound B2. The temperature was 30° C. in the Compound B2 solution before sodium hydroxide was added. The addition time for sodium hydroxide was approximately 20 minutes, and during the addition time the temperature increased to approximately 55° C. The solution was then diluted with water to a total volume of 850 mL. Hydrochloric acid (17.5%) was then added until the solution was slightly turbid, and the solution was seeded with Compound A (0.9 g). The slurry was stirred in 45 minutes before hydrochloric acid (17.5%) was added until pH was about 7. The slurry was then cooled to 15° C. over night. The next day the slurry was filtered, and the filter cake was washed with methanol and then dried in a vacuum oven.

The dried product was analyzed by HPLC, and the level of the impurity Compound 1 was 0.09%.

Process of the Invention:
Sodium hydroxide (50%, 145 mL) was added to water (250 mL). The temperature was 40° C. in the diluted sodium hydroxide solution before the Compound B2 solution was added. The addition time for the over-acylated Compound B solution was approximately 30 minutes, and during the addition time the temperature increased to approximately 55° C. The solution was then diluted with a little amount of water to a total volume of 850 mL. Hydrochloric acid (17.5%) was then added until the solution was slightly turbid, and the solution was seeded with Compound A (0.9 g). The slurry was stirred for 45 minutes before hydrochloric acid (17.5%) was added until pH was about 7. The slurry was then cooled to 15° C. over the night. The next day the slurry was filtered, and the filter cake was washed with methanol and then dried in a vacuum oven. The dried product was analysed by HPLC, and the level of the impurity Compound 1 was only 0.02%.

Example 2

Comparing the Amount of Generated Impurity Compound 1 in Solution

Two acetylation reactions were done in similar way as described in Example 1. Some changes compared to Example 1 were done for generating high level of precursors of the epoxide Compound 2.

Comparative Process of the State of the Art:
Sodium hydroxide (50%, 200 mL) was added to the solution containing over-acylated Compound B (B2 solution). The solution was then diluted with water to a total volume of 870-880 mL. HPLC-analysis of the solution prior to crystallization showed that the level of Compound 1 was 5.8%.

Process of the Invention:
Sodium hydroxide (50%, 170 mL) was added to water (280 mL). Compound B2 solution was then added to the diluted sodium hydroxide. The solution was then diluted with water to a total volume of 870-880 mL. HPLC-analysis of the solution prior to crystallization showed that the level of Compound 1 was 0.3%, showing that considerably less Compound 1 is generated when using the process of the invention than when using the state of the art process, affecting the overall yield positively.

The invention claimed is:

1. A process for preparation of an N-acylated monomeric compound selected from 5-acetamido-N,N'-bis(2,3-dihydroxypropyl)-2,4,6-triiodoisophthalamide (Compound A) and N,N'-bis(2,3-dihydroxypropyl)-5-formamido-2,4,6-triiodoisophthalamide (Compound C) comprising a step wherein Compound B2,

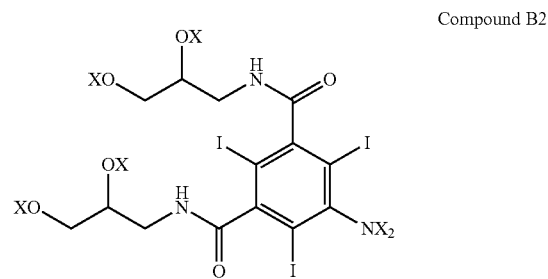

Compound B2 wherein each X individually denotes a hydrogen or an acyl group, provided that at least one of the X-groups attached to the nitrogen is an acyl group;
is subjected to deacylation of the acylated hydroxyl groups by adding the Compound B2 to an aqueous solution of a deacylating agent.

2. A process as claimed in claim 1 wherein the deacylating agent is an inorganic base.

3. A process as claimed in claim 1 wherein Compound B2 is added to the deacylating agent in the form of a solution.

4. A process as claimed in-claim 1 wherein Compound B2 is Compound B3

Compound B3

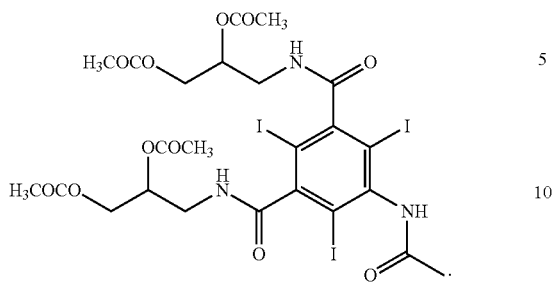

5. A process as claimed in claim 4 wherein the generation of the impurity Compound 1

Compound 1

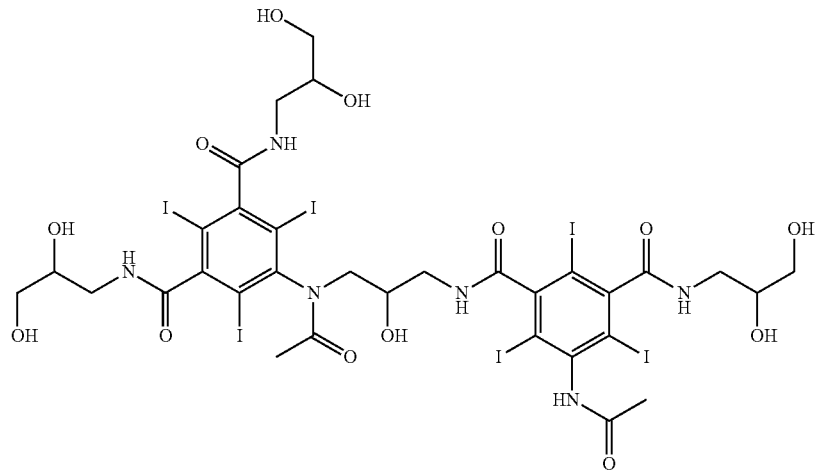

is minimized.

6. A process as claimed in claim 1 wherein the pH of the mixed solution of Compound B2 and the deacylating agent is reduced from about 14 to about 11-13 during the addition to the deacylating agent.

7. A process as claimed in claim 1 wherein the compound B2 is added to the aqueous solution of the deacylating agent over a period of 0.5-2 hours either in several small portions or continuously.

8. A process as claimed in claim 1 comprising a first step of acylating Compound B Compound B

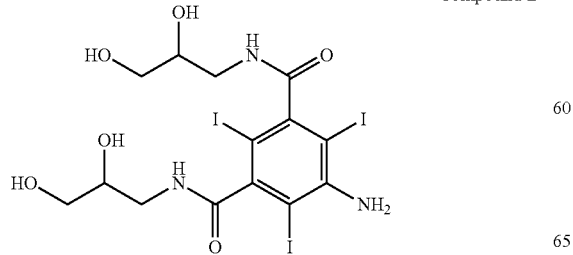

to prepare compound B2;
followed by a step wherein a solution of Compound B2 is subjected to deacylation of the acylated hydroxyl groups by adding the compound B2 to an aqueous solution of a deacylating agent.

9. A dried product of Compound A comprising 0.08 weight % or less of Compound 1,

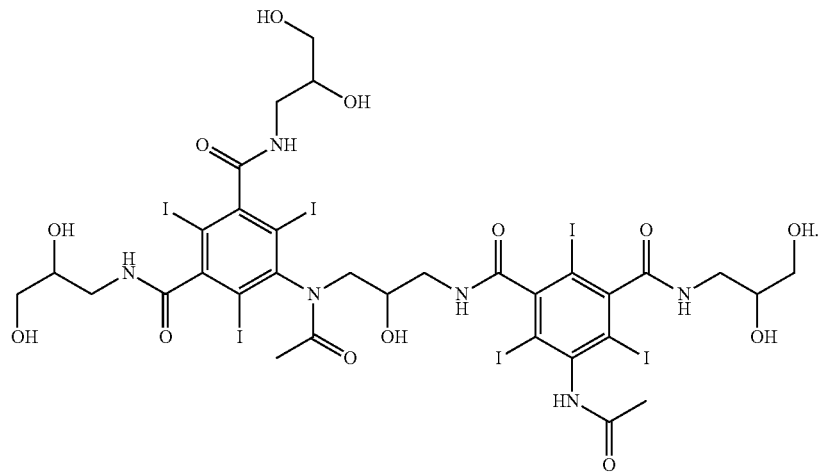

Compound 1

10. A process for preparing a contrast agent comprising the process for preparation of Compound A or Compound C as claimed in claim 1.

11. A process as claimed in claim 10 wherein the contrast agent is Iodixanol, Iohexol or Ioformiol.

* * * * *